United States Patent
LaVallie et al.

(10) Patent No.: US 7,026,445 B2
(45) Date of Patent: Apr. 11, 2006

(54) HUMAN SDF-5 PROTEIN AND COMPOSITIONS

(75) Inventors: Edward R. LaVallie, Harvard, MA (US); Lisa A. Racie, Acton, MA (US); Gary Hattersley, Stow, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 08/949,904

(22) Filed: Oct. 15, 1997

(65) Prior Publication Data

US 2003/0175855 A1  Sep. 18, 2003

Related U.S. Application Data

(63) Continuation-in-part of application No. 08/848,439, filed on May 8, 1997, which is a continuation-in-part of application No. 08/796,153, filed on Feb. 6, 1997, now abandoned.

(51) Int. Cl.
- *C07K 1/00* (2006.01)
- *C07H 21/02* (2006.01)
- *C12P 27/06* (2006.01)
- *C12N 1/20* (2006.01)

(52) U.S. Cl. .............. 530/350; 530/361; 536/23.1; 435/69.1; 435/252.3

(58) Field of Classification Search ........... 536/23.1; 530/412; 435/69.1, 320.1, 325
See application file for complete search history.

(56) References Cited

FOREIGN PATENT DOCUMENTS

WO  WO 93/00441  1/1993
WO  WO 98/13493  4/1998

OTHER PUBLICATIONS

Freshney (Culture of Animal Cells, A Manual of Basic Technique, Alan R. Liss, Inc., NY, p. 4).*
Dermer (Bio/Technology, 12:320).*
Bowie et al (Science, 1990, 257:1306-1310).*
Lazar et al (Mol. Cell. Bio., 1988, 8:1247-1252).*
Burgess et al (J. Cell Bio., 1990, 111:2129-2138).*
Bork et al (Benome Research, 2000, 10:398-400).*
Shirozu et al (genomics, 1996, 37:273-280).*
Bhanot et al., Nature 382:225-230 (1996).
Wang et al., J. Biol. Chem. 271:4468-4476 (1996).
Metsaranta et al., Dev. Dynamics 204:202-210 (1996).
Li et al., Genes Develop. 9:2821-2830 (1996).
Pacifici et al., Matrix Biol. 14:689-698 (1995).
Jang et al., J. Virol. 63:1651-1660 (1989).
Finch et al., PNAS USA 94:6770-6775 (1997).
Gori, F. et al., "Cloning and Characterization of a Novel WD-40 Repeat Protein that Dramatically Accelerates Osteoblastic Differentiation," Journal of Biological Chemistry, Dec. 7, 2001, 46515-22, 276(49), American Society for Biochemistry and Molecular Biology, Inc.
Kearns, A. et al., "Cloning and Characterization of a Novel Protein Kinase that Impairs Osteoblast Differentiation in Vitro," Journal of Biological Chemistry, Nov. 9, 2001, 42213-8, 276(45), American Society for Biochemistry and Molecular Biology, Inc.
Rosen, V. et al., "Responsiveness of Clonal Limb Bud Cell Lines to Bone Morphogenetic Protein 2 Reveals a Sequential Relationship Between Cartilage and Bone Cell Phenotypes," Journal of Bone and Mineral Research, Nov. 1994, 1759-68, 9(11), Mary Ann Liebert, Inc.

* cited by examiner

*Primary Examiner*—Susan Ungar
(74) *Attorney, Agent, or Firm*—Nixon Peabody LLP; Raymond Van Dyke

(57) ABSTRACT

Purified human SDF-5 proteins and processes for producing them are disclosed. DNA molecules encoding the human SDF-5 proteins are also disclosed. The proteins may be used in regulating the binding of Wnt genes to their receptor. In preferred embodiments, the proteins may be used for inducing formation, growth, differentiation, proliferation and/or maintenance of chondrocytes and/or cartilage tissue, and for other tissue repair, such as pancreatic tissue repair.

3 Claims, No Drawings

HUMAN SDF-5 PROTEIN AND COMPOSITIONS

RELATED APPLICATIONS

The present application is a continuation-in-part of application Ser. No. 08/848,439, filed May 8, 1997, which is a continuation-in-part of application Ser. No. 08/796,153, filed on Feb. 6, 1997 now abandoned.

The present invention relates to novel members of the Frazzled protein family, DNA encoding them, and processes for obtaining them. These proteins may be used to induce expression of factors in and/or differentiation of tissue and organs, and particularly, inducing formation, growth, differentiation, proliferation and/or maintenance of chondrocytes and/or cartilage tissue. Thus, these proteins may be useful in the treatment of cartilage disorders, such as osteoarthritis, rheumatoid arthritis and articular cartilage defects, and in the enhancement and/or inhibition of cellular formation, growth, differentiation, proliferation and/or maintenance of other tissue and organs, for example pancreatic, liver, spleen, lung, kidney and/or other tissue. These proteins may also be used for augmenting the activity of other tissue regenerating and differentiation factors. The protein has been named human SDF-5 by the inventors.

BACKGROUND OF THE INVENTION

The search for the molecule or molecules responsible for the formation, proliferation, differentiation and maintenance of tissue and organs, such as cartilage and connective tissues, has been extensive as there is a tremendous need for factors useful for treating conditions involving degradation or damage to these tissues, such as osteoarthritis.

The structures of several proteins in the family designated as Frazzled, have previously been elucidated. The present invention relates to a family of proteins designated as Frazzled, which family shares homology to the ligand binding domain of the Frizzled proteins. Frizzled protein family members have been shown to bind to the Wingless (Wg) protein in *Drosophila*. Bhanot et al., *Nature*, 382:225–230 (1996). In mammals and other species, the Frizzled family of proteins are membrane bound receptor molecules which have been shown to bind to proteins produced by the family of Wnt genes. Wang et al., *J. Biol. Chem.*, 271:4468–4476 (1996). Wnt genes have been determined to be expressed in tissue and organs including the pancreas, lung, liver, kidney, and brain.

SUMMARY OF THE INVENTION

The inventors herein have surprisingly discovered that members of the Frazzled protein family are able to induce the formation of chondrocytes and/or cartilage tissue. Accordingly, the present invention provides methods for inducing formation of chondrocyte and/or cartilage tissue comprising administering to progenitor cells a composition comprising at least one protein which is a member of the Frazzled protein family. In preferred embodiments, the composition may comprise a protein having the amino acid sequence of SEQUENCE ID NO:2 from amino acid 1, 18, 19, 20, 21, 22, 23, 24 or 25 to 295; in a preferred embodiment, the invention comprises a protein having the amino acid sequence of SEQUENCE ID NO:1 from amino acid 21 to 295 or SEQUENCE ID NO:3 from amino acid 1 to 275. In one embodiment, the method comprises administering the composition to a patient in vivo. Alternatively, the method may comprise administering the composition to cells in vitro and recovering chondrocytes and/or cartilage tissue, which may subsequently be administered to a patient. The composition may further comprise a suitable carrier for administration.

The present invention also provides novel DNA sequences encoding novel members of the Frazzled and Frizzled protein families. In particular embodiments, the present invention provides novel DNA sequences encoding the Frazzled protein known as human SDF-5. The nucleotide sequences, and the corresponding amino acid sequences encoded by these DNA sequences, are provided in the Sequence Listings. In particular, the present invention comprises isolated DNA sequence encoding a human SDF-5 protein comprising a DNA sequence selected from the group consisting of: nucleotides #256, 307, 310, 313, 316, 319, 322, 325 or 328 to #1140 of SEQ ID NO: 1; or nucleotides encoding amino acids #1, 18, 19, 20, 21, 22, 23, 24 or 25 to #295 of SEQ ID NO: 2; or nucleotides encoding amino acids #1 to #275 of SEQ ID NO: 3, as well as fragments and variants of the above sequences which are readily obtainable from the above and which maintain Frazzled activity. The present invention further comprises sequences which hybridize to these sequences under stringent hybridization conditions and encode a protein which exhibits Frazzled activity.

In other embodiments, the present invention comprises vectors comprising the above DNA molecules in operative association with an expression control sequence therefor, as well as host cells transformed with these vectors. In yet other embodiments, the present invention comprises methods for producing purified human SDF-5 proteins, novel human SDF-5 proteins, and compositions containing the human SDF-5 proteins. These methods may comprise the steps of: culturing a host cell transformed with a DNA sequence encoding a human SDF-5 protein such as described above; and recovering and purifying said human SDF-5 protein from the culture medium. The present invention further comprises the purified human SDF-5 polypeptide produced by the above methods, as well as purified human SDF-5 polypeptides comprising an amino acid sequence encoded by the above DNA sequences. The proteins of the present invention may comprise the amino acid sequence from amino acid #1, 18, 19, 20, 21, 22, 23, 24 or 25 to #295 of SEQ ID NO:2; the amino acid sequence from amino acid #1 to #275 of SEQ ID NO:3; or a human SDF-5 protein having a molecular weight of about 30 to about 35 kd, said protein comprising the amino acid sequence of SEQ ID NO: 2 or 3 and having the ability to regulate the transcription of one or more genes.

The present invention also includes methods for inducing the formation or maintenance of cartilaginous tissue in a patient, comprising administering to the patient an effective amount of a composition comprising an SDF-5 protein. Said composition may further comprise one or more bone morphogenetic proteins (BMP), preferably a BMP selected from BMP-2, BMP-4, BMP-7, MP52, BMP-12 and BMP-13, most preferably BMP-2. The methods may be used to treat patients suffering from osteoarthritis, or an articular cartilage defect or damage.

Description of Sequences

SEQ ID NO: 1 human SDF-5 DNA
SEQ ID NO: 2 human SDF-5 protein
SEQ ID NO: 3 human SDF-5 mature protein Description of Deposits A cDNA insert pSDF-5, which contains the human SDF-5 DNA coding sequence was inserted into an ampicillin *E. coli* strain and was deposited with the American Type Culture Collection, 12301 Parklawn Drive, Rockville, Md. 20852 on Feb. 4, 1997. This deposit has been accorded the accession number ATCC 98314. This deposit meets the requirements of the Budapest Treaty.

DETAILED DESCRIPTION OF THE INVENTION

As used herein, the term "Frazzled protein" refers to the human Frazzled protein members which share sequence homology to the extracellular binding domains of the Frizzled protein family, including Hfz3, Hfz5, and Hfz7, as well as other human Frazzled proteins, and Frazzled protein members found in other species and share sequence homology to Frizzled proteins from other species, such as those described in Wang et al., Wang et al., *J. Biol. Chem.*, 271:4468–4476 (1996). One specific member of the Frazzled protein family is the human SDF-5 protein, having the amino acid sequence specified in SEQUENCE ID NO:2, as well as homologues of this protein found in other species; and other proteins which are closely related structurally and/or functionally to SDF-5. It is also known that Frazzled related proteins also exist in other species, including family members in *Drosophila, Xenopus, C. elegans*, zebrafish, as well as in rats, mice and humans. "Frazzled proteins" also includes variants of the Frazzled proteins, such as allelic variants or variants induced by mutagenesis or deletions, and fragments of Frazzled or Frizzled proteins which variants and fragments retain Frazzled activity, preferably, the ability to bind to proteins, such as the Wnt proteins, which would otherwise bind to membrane bound receptors, such as the Frizzled proteins.

As used herein, the term "Frazzled activity" refers to one or more of the activities which are exhibited by the Frazzled proteins of the present invention. In particular, "Frazzled activity" includes the ability to bind to Wnt proteins, and may thus include the ability to regulate the binding of Wnt proteins to protein receptors such as the Frizzled protein receptors. "Frazzled activity" may further include the ability to regulate the formation, differentiation, proliferation and/or maintenance of cells and/or tissue, for example connective tissue, organs and wound healing. In particular, "Frazzled activity" may include the ability to enhance and/or inhibit the formation, growth, proliferation, differentiation and/or maintenance of chondrocytes and/or cartilage tissue. "Frazzled activity" also includes the activities of Frazzled protein in the assays described herein.

Thus, the present invention includes protein variants and functional fragments of the amino acid sequence of the human SDF-5 proteins shown in SEQ ID NO: 2 or 3 which retain Frazzled activity. The present invention also includes antibodies to a purified human SDF-5 protein such as the above. The compositions of the present invention comprise a therapeutic amount of at least one of the above human SDF-5 proteins.

It is expected that human SDF-5 protein, as expressed by mammalian cells such as CHO cells, exists as a heterogeneous population of active species of human SDF-5 protein with varying N-termini. Based in part upon the Von Heginje signal peptide prediction algorithm, the first 17 to 24 amino acids appear to be involved in signalling for the secretion of the mature peptide. It is expected that active species may optionally include the signal peptide and will include amino acid sequences beginning with amino acid residues #1, 18, 19, 20, 21, 22, 23, 24 or 25 of SEQ ID NO:2. Thus, it is expected that DNA sequences encoding active human SDF-5 proteins include those comprising nucleotides #256, 307, 310, 313, 316, 319, 322, 325 or 328 to #1140 of SEQ ID NO: 1. Accordingly, active species of SDF-5 are expected to include those comprising amino acids #1, 18, 19, 20, 21, 22, 23, 24 or 25 to #295 of SEQ ID NO:2.

In yet another embodiment, the present invention comprises a method of altering the regulation of genes in a patient in need of same comprising administering to said patient an effective amount of the above compositions. The alteration of regulation of pancreatic genes may be accomplished by stimulating or inhibiting binding by Wnt proteins of receptor proteins, for example, binding between the human SDF-5 protein of the present invention and the Wnt protein. Thus, the human SDF-5 protein family may be capable of regulating the binding interaction of Wnt genes to receptor proteins, such as Frizzled receptor proteins.

The present invention also encompasses hybrid or fusion vectors comprising the coding DNA sequences of the present invention and other Frazzled encoding sequences, linked to a tissue specific or inducible regulatory sequence, such as a promoter or operator. In a preferred embodiment of the invention, the coding sequence for human SDF-5 protein is operably linked to one or more promoters, enhancers and/or other regulatory elements from genes which are selectively expressed in chondrocyte cells and/or cartilage tissue. For example, the collagen type II enhancer promoter, which is known to be expressed in cartilage during mesenchymal condensation and cartilage. Metsaranta et al., *Dev. Dynamics*, 204:202–210 (1996); Li et al., *Genes Develop.*, 9:2821–2830 (1996). Another regulatory element useful in the present invention is the tenascin C promoter. Tenascin C is expressed in articular cartilage. Pacifici et al., *Matrix Biol.*, 14:689–698. Additionally, the DNA sequence encoding human SDF-5 may be operatively linked to one or more regulatory sequences from proteoglycan core proteins, which are selectively produced in chondrocytes and/or cartilage tissue. In other preferred embodiments of the invention, the coding sequence for human SDF-5 protein is operably linked to the promoter isolated from the IDX gene. This promoter is selectively expressed in pancreatic cells and tissue. Thus, a hybrid DNA vector in which the IDX promoter is operably linked to a DNA sequence encoding a human SDF-5 protein is useful for selective expression of the protein in pancreatic tissue, for example for the treatment of a pancreatic disorder or for altering the regulation of pancreatic genes in a patient, for example by stimulating or inhibiting binding by Wnt proteins of its receptor protein, for example by binding between the expressed human SDF-5 protein and the Wnt protein. Vectors using other tissue-selective regulatory elements and inducible regulatory elements may also be useful for the selective or inducible expression of the human SDF-5 proteins of the present invention.

Another aspect of the invention provides pharmaceutical compositions containing a therapeutically effective amount of human SDF-5 protein, in a pharmaceutically acceptable vehicle or carrier. These compositions of the invention may be used in the formation of chondrocytes and/or cartilage tissue phenotype. These compositions may further be utilized in order to enhance and/or inhibit the formation, growth, proliferation, differentiation and/or maintenance of beta cells, and other cell types typically found in the islets of Langerhans or other pancreatic cells, as well as other organ tissues such as liver, spleen, brain, lung, cardiac, and kidney tissue. The compositions comprising human SDF-5 protein may be used to treat precursor or stem cells, such as pancreatic stem cells, which are able to differentiate into cells which comprise differentiated tissue or organs, such as pancreatic cells, in order to enhance the formation, differentiation, proliferation and/or maintenance of such cells, tissue or organs. Methods for forming and maintaining such cells are described, for example, in WO93/00441, the disclosure of which is hereby incorporated herein by reference.

The compositions of the invention may comprise, in addition to a human SDF-5 protein, other therapeutically useful agents including growth factors such as epidermal growth factor (EGF), fibroblast growth factor (FGF), transforming growth factor (TGF-α and TGF-β), activins, inhibins, bone morphogenetic proteins (BMP), and insulin-like growth factor (IGF). The compositions may also include an appropriate matrix for instance, for supporting the composition and providing a surface for chondrocytic cell, and/or cartilaginous tissue growth. The matrix may provide slow release of the human SDF-5 protein and/or the appropriate environment for presentation thereof.

The human SDF-5 protein containing compositions may be employed in methods for treating a number of tissue defects, and healing and maintenance of various types of tissues and wounds. The tissues and wounds which may be treated include cartilage, but may also include epidermis, nerve, muscle, including cardiac muscle, other connective tissue, such as bone, tendon and ligament and other tissues and wounds, and other organs such as pancreas, liver, spleen, lung, brain, cardiac, and kidney tissue. These methods, according to the invention, entail administering to a patient needing such tissue formation, wound healing or tissue repair, an effective amount of human SDF-5 protein. The human SDF-5 containing compositions may also be used to treat or prevent such conditions as rheumatoid arthritis, osteoarthritis, and other abnormalities of cartilaginous, or other organs or tissues, such as pancreas, liver, spleen, lung, cardiac, brain, and kidney tissue, and other tissues and organs. These methods may also entail the administration of a protein of the invention in conjunction with administration of at least one other protein, for example growth factors including EGF, FGF, TGF-α, TGF-β, BMP, activin, inhibin and IGF.

Still a further aspect of the invention are DNA sequences coding for expression of human SDF-5 protein. Such sequences include the sequence of nucleotides in a 5' to 3' direction illustrated in SEQ ID NO: 1, DNA sequences which, but for the degeneracy of the genetic code, are identical to the DNA sequence SEQ ID NO: 1, and encode the protein of SEQ ID NO: 2 or 3. Further included in the present invention are DNA sequences which hybridize under stringent conditions with the DNA sequence of SEQ ID NO: 1 and encode a protein having the ability to bind to one or more Wnt proteins, and/or which have the ability to enhance and/or inhibit the formation, growth, proliferation, differentiation, maintenance of pancreatic cells, such as insulin-producing beta cells, or other organ tissues such as liver, spleen, lung, cardiac, brain and kidney tissue. Preferred DNA sequences include those which hybridize under stringent conditions [see, T. Maniatis et al, *Molecular Cloning (A Laboratory Manual)*, Cold Spring Harbor Laboratory (1982), pages 387 to 389]. It is generally preferred that such DNA sequences encode a polypeptide which is at least about 80% homologous, and more preferably at least about 90% homologous, to the mature human SDF-5 amino acid sequence shown in SEQ ID NO:2 or 3. Finally, allelic or other variations of the sequences of SEQ ID NO: 1, whether such nucleotide changes result in changes in the peptide sequence or not, but where the peptide sequence still has Frazzled activity, are also included in the present invention. The present invention also includes functional fragments of the DNA sequence of human SDF-5 proteins shown in SEQ ID NO: 1 which encode a polypeptide which retains the activity of Frazzled protein. The determination whether a particular variant or fragment of the human SDF-5 protein of the present invention, such as those shown in SEQ ID NO: 2 or 3 maintain Frazzled activity, is routinely performed using the assays described herein.

The DNA sequences of the present invention are useful, for example, as probes for the detection of mRNA encoding other Frazzled protein in a given cell population. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a recombinant human SDF-5 protein of the invention in which a cell line transformed with a DNA sequence encoding human SDF-5 protein in operative association with an expression control sequence therefor, is cultured in a suitable culture medium and human SDF-5 protein is recovered and purified therefrom. This process may employ a number of known cells both prokaryotic and eukaryotic as host cells for expression of the polypeptide. The vectors may also be used in gene therapy applications. In such use, the vectors may be transfected into the cells of a patient ex vivo, and the cells may be reintroduced into a patient. Alternatively, the vectors may be introduced into a patient in vivo through targeted transfection.

In a preferred embodiment of the invention, vectors are prepared using one or more non-native regulatory elements, such as promoters and/or enhancers operatively associated with the coding sequence for human SDF-5, in order to achieve expression of human SDF-5 in desired cell tissue and/or at a desired time in development. For example, a vector may be constructed using the promoter element from the well-characterized IDX gene, which is known to be constitutively expressed in pancreatic cells, including beta cells, during development. By operatively associating the promoter from the IDX gene with the coding sequence for Frazzled, and transforming suitable cells, such as pancreatic stem cells as described in WO93/00441, one can express human SDF-5 in these cells, thus promoting the desired effects of formation, growth, proliferation, differentiation and/or maintenance of cells such as pancreatic beta cells which are able to secrete insulin, either in in vitro culture or in vivo.

Still a further aspect of the invention are human SDF-5 proteins or polypeptides. Such polypeptides are characterized by having an amino acid sequence including the sequence illustrated in SEQ ID NO: 2 or 3, variants of the amino acid sequence of SEQ ID NO: 2 or 3, including naturally occurring allelic variants, and other variants in which the protein retains Frazzled ability, for example, the ability to enhance and/or inhibit the formation, growth, proliferation, differentiation and/or maintenance of chondrocytes and/or cartilage tissue and/or pancreatic or other organ tissue, such as liver, spleen, lung, cardiac, brain and kidney tissue, characteristic of Frazzled protein. Preferred polypeptides include a polypeptide which is at least about 80% and more preferably at least about 90% homologous to the mature human SDF-5 amino acid sequences shown in SEQ ID NO: 2 and 3. Finally, allelic or other variations of the sequences of SEQ ID NO: 2 or 3, whether such amino acid changes are induced by mutagenesis, chemical alteration, or by alteration of DNA sequence used to produce the polypeptide, where the peptide sequence still has Frazzled activity, are also included in the present invention. The present invention also includes fragments of the amino acid sequence of human SDF-5 shown in SEQ ID NO:2 or 3 which retain the activity of Frazzled protein. One skilled in the art can readily produce such variations and fragments of the human SDF-5 protein using techniques known in the art, and can readily assay them for activity, as described in the examples herein.

The purified proteins of the present inventions may be used to generate antibodies, either monoclonal or polyclonal, to human SDF-5 proteins and/or other related proteins, using methods that are known in the art of antibody production. Thus, the present invention also includes antibodies to human SDF-5 and/or other Frazzled proteins. The antibodies may be useful for purification of human SDF-5 proteins, or for inhibiting or preventing the effects of Frazzled proteins either in vitro or in vivo. The human SDF-5 proteins may be useful for inducing the growth and/or differentiation of embryonic cells and/or stem cells. Thus, the proteins or compositions of the present invention may also be useful for treating cell populations, such as embryonic cells or stem cell populations, to enhance, enrich or to inhibit the growth and/or differentiation of the cells. For example, the human SDF-5 proteins may be useful for treating cell populations to enhance and/or inhibit the formation, differentiation, proliferation and/or maintenance of chondrocytes, cartilaginous tissue and/or other cells such as cells of pancreatic or other tissue or organ phenotype. The treated cell populations may be useful for, among other things, gene therapy applications, as described below.

It is of particular interest that the human SDF-5 gene appears to encode a secreted factor, thus providing soluble receptors which may be capable of binding with the Wnt proteins, thus initiating and/or blocking signal transduction by the Wnt proteins. Thus, the human SDF-5 gene family may be capable of regulating the binding interaction of Wnt genes to receptor proteins, such as the Frizzled receptor proteins. The potential signal transduction regulation activities of these proteins, along with the presence and/or expression of Wnt genes in pancreas and other organs suggests that human SDF-5 protein is an important regulator of differentiation of tissue and organs, and may be involved in the induction, formation, growth, differentiation, proliferation and/or maintenance of tissues and organs. Thus, the proteins of the present invention may be useful in wound healing, tissue and organ repair and regeneration processes, as well as in differentiation of tissue, for example in embryonic development. In particular, it has been observed by the inventors that the human SDF-5 protein may be useful for the induction, formation, growth, differentiation, proliferation and/or maintenance and repair of chondrocytes and/or cartilage tissue. Thus, these proteins, and compositions containing them, may be useful in the treatment of cartilage disorders, such as osteoarthritis, rheumatoid arthritis and articular cartilage defects, and in the enhancement and/or inhibition of cellular formation, growth, differentiation, proliferation and/or maintenance, for example formation of chondrocytes and/or cartilage tissue.

The human SDF-5 proteins provided herein include factors encoded by the sequences similar to those of SEQ ID NO: 1, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2 or 3. These sequences, by virtue of sharing primary, secondary, or tertiary structural and conformational characteristics with human SDF-5 polypeptides of SEQ ID NO: 2 or 3 may possess biological properties in common therewith. Thus, these modifications and deletions of the native human SDF-5 may be employed as biologically active substitutes for naturally-occurring human SDF-5 polypeptides in therapeutic processes. It can be readily determined whether a given variant or fragment of human SDF-5 maintains the biological activity of Frazzled by subjecting both human SDF-5 and the variant or fragment of human SDF-5 to the assays described herein; in addition the variant or fragment may be used in a competitive binding assay to test for binding to the Wnt gene.

Other specific mutations of the sequences of human SDF-5 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Such variants of human SDF-5 are within the present invention. Additionally, bacterial expression of human SDF-5 proteins will result in production of a non-glycosylated protein, even if the glycosylation sites are left unmodified. Such bacterially produced versions of human SDF-5 are within the present invention.

The present invention also encompasses the novel DNA sequences, free of association with DNA sequences encoding other proteinaceous materials, and coding for expression of human SDF-5 proteins. These DNA sequences include those depicted in SEQ ID NO: 1 in a 5' to 3' direction and those sequences which hybridize thereto under stringent hybridization conditions [for example, 0.1×SSC, 0.1% SDS at 65° C.; see, T. Maniatis et al, *Molecular Cloning (A Laboratory Manual)*, Cold Spring Harbor Laboratory (1982), pages 387 to 389] and encode a protein having Frazzled activity. These DNA sequences also include those which comprise the DNA sequence of SEQ ID NO: 1 and those which hybridize thereto under stringent hybridization conditions and encode a protein having Frazzled activity.

Similarly, DNA sequences which code for human SDF-5 proteins coded for by the sequences of SEQ ID NO: 1, or human SDF-5 proteins which comprise the amino acid sequence of SEQ ID NO: 2 or 3, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 which are caused by point mutations or by induced modifications (including insertion, deletion, and substitution) to enhance the activity, half-life or production of the polypeptides encoded are also encompassed in the invention.

Another aspect of the present invention provides a novel method for producing human SDF-5 proteins. The method of the present invention involves culturing a suitable cell line, which has been transformed with a DNA sequence encoding a human SDF-5 protein of the invention, under the control of known regulatory sequences. The transformed host cells are cultured and the human SDF-5 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas*, other *bacilli* and the like may also be employed in this method. For expression of the protein in bacterial cells, DNA encoding the signal peptide of Frazzled is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel human SDF-5 polypeptides. Preferably the vectors contain the full novel DNA sequences described above which encode the novel factors of the invention. Additionally, the vectors contain appropriate expression control sequences permitting expression of the Frazzled protein sequences. Alternatively, vectors incorporating modified sequences as described above are also embodiments of the present invention. Additionally, the sequence of SEQ ID NO:1 or other sequences encoding human SDF-5 proteins could be manipulated to express a mature human SDF-5 protein by deleting human SDF-5 signal peptide sequences and replacing them with sequences encoding the complete signal peptides of other Frazzled proteins or other suitable propeptides. Thus, the present invention includes chimeric DNA molecules encoding a signal peptide from a member of the Frazzled family linked in correct reading frame to a DNA sequence encoding a human SDF-5 polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

In order to produce rat, human or other mammalian SDF-5 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human SDF-5 is contemplated to be stably transformed mammalian cells.

One skilled in the art can construct mammalian expression vectors by employing the sequence of SEQ ID NO: 1, or other DNA sequences encoding SDF-5 proteins or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'-

CTGCAGGCGAGCCTGAATTCCTCGAGCCATCATG-3'
   PstI    Eco RI XhoI

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECAT1 [S. K. Jung, et al, *J. Virol* 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
5'CGAGGTTAAAAAACGTCTAGGCCCCCCGAACCACGGGGACGTGGTTT
TCCTTT
 TaqI

GAAAAACACGATTGC-3'
        XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the human SDF-5 DNA sequences. For instance, human SDF-5 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of human SDF-5 proteins. Additionally, the sequence of SEQ ID NO:1 other sequences encoding human SDF-5 proteins can be manipulated to express a mature human SDF-5 protein by deleting human SDF-5 encoding signal peptide sequences and replacing them with sequences encoding the complete signal peptides of other proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified human SDF-5 coding sequence could then be inserted into a known bacterial vector using procedures such as described in T. Taniguchi et al., *Proc. Natl. Acad. Sci. USA,* 77:5230–5233 (1980). This exemplary bacterial vector could then be transformed into bacterial host cells and a protein expressed thereby. For a strategy for producing extracellular expression of human SDF-5 proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a human SDF-5 protein of the invention in mammalian cells may involve the construction of cells containing multiple copies of the heterologous human SDF-5 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.,* 159: 601–629 (1982). This approach can be employed with a number of different cell types.

For example, a plasmid containing a DNA sequence for a human SDF-5 protein of the invention in operative association with other plasmid sequences enabling expression thereof and the DHFR expression plasmid pAdA26SV(A)3 [Kaufman and Sharp, *Mol. Cell. Biol.,* 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 μM MTX) as described in Kaufman et al., *Mol Cell Biol.,* 5:1750 (1983). Transformants are cloned, and biologically active human SDF-5 expression is monitored by assay in one of the assays described herein. Human SDF-5 protein expression should increase with increasing levels of MTX resistance. Human SDF-5 polypeptides are characterized using standard techniques known in the art such as pulse labeling with [35S] methionine or cysteine and polyacrylamide gel electrophoresis. Similar procedures can be followed to produce other related SDF-5 proteins.

An SDF-5 protein of the present invention, which demonstrates Frazzled activity, has application in the induction, formation, growth, differentiation, proliferation and/or maintenance and healing of cells and tissues such as chondrocytes and/or cartilaginous tissue, as well as pancreatic tissue, and other organ tissues, in humans and other animals. Such a preparation employing human SDF-5 protein may have prophylactic use in treatment of rheumatoid arthritis and osteoarthritis and traumatic injury to cartilage, as well as preventing pancreatic tumors, diabetes and other pancreatic tissue disorders. De novo formation of beta cells, islet of Langerhans cells, and other cells of pancreatic phenotype, induced by a Frazzled protein contributes to the repair of congenital, trauma induced, or oncologic tissue defects or conditions. Human SDF-5 protein may also be used in the treatment of pancreatic disease, and in other tissue and organ repair processes. Such agents may provide an environment to attract suitable stem cells, stimulate growth and proliferation of pancreas-forming cells or induce differentiation of progenitors of pancreas-forming cells, and may also support the regeneration of other tissues and organs. Human SDF-5 polypeptides of the invention may also be useful in the treatment of organ disorders such as pancreitis or diabetes.

The proteins of the invention may also be used in wound healing and in related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal, astrocytic and/or glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, connective tissue, such as bone, cartilage, tendon and ligament, and other organs such as pancreas, liver, spleen, lung, cardiac, brain and kidney tissue. The proteins of the present invention may also have value as a dietary supplement, or as additives for cell culture media. For this use, the proteins may be used in intact form, or may be predigested to provide a more readily absorbed supplement.

The proteins of the invention may also have other useful properties characteristic of the Frazzled family of proteins. Such properties include angiogenic, chemotactic and/or chemoattractant properties, and effects on cells including differentiation responses, cell proliferative responses and responses involving cell adhesion, migration and extracellular matrices. These properties make the proteins of the invention potential agents for wound healing, reduction of fibrosis and reduction of scar tissue formation. The proteins of the invention may also be useful for the induction of formation of cells capable of secreting valuable hormones, such as insulin, glucagon or other endocrine or exocrine hormones.

A further aspect of the invention is a therapeutic method and composition for treating disorders of cartilage and connective tissue, as well as disorders of the pancreas, diabetes, and other conditions related to pancreatic tissue disorders or diseases. The invention further comprises therapeutic methods and compositions for wound healing and tissue repair. Such compositions comprise a therapeutically effective amount of at least one human SDF-5 protein of the present invention in admixture with a pharmaceutically acceptable vehicle, carrier or matrix. It is further contemplated that compositions of the invention may increase neuronal and glial cell survival and therefore be useful in transplantation and treatment of conditions exhibiting a decrease in neuronal survival.

It is expected that the proteins of the invention may act in concert with or perhaps synergistically with other related proteins and growth factors. Further therapeutic methods and compositions of the invention therefore comprise a therapeutic amount of at least one human SDF-5 protein of the invention with a therapeutic amount of at least one other protein, such as a member of the TGF-β superfamily of proteins, which includes the bone morphogenetic proteins (BMPs), growth and differentiation factors (GDFS) and other proteins. BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO95/16035, or BMP-15, disclosed in PCT application WO96/36710 or BMP-16, disclosed in co-pending patent application Ser. No. 08/715,202, filed Sep. 18, 1996.

Other compositions which may also be useful include Vgr-2, and any of the growth and differentiation factors [GDFs], including those described in PCT applications WO94/15965; WO94/15949; WO95/01801; WO95/01802; WO94/21681; WO94/15966; and others. Also useful in the present invention maybe BIP, disclosed in WO94/01557; and MP52, disclosed in PCT application WO93/16099. The disclosures of all of the above applications are hereby incorporated by reference for the disclosure contained therein. In a preferred embodiment, the SDF-5 is combined with a protein BMP-2, BMP-7, MP52, BMP-12 or BMP-13.

The composition may include other agents and growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), leukemia inhibitory factor (LIF/HILDA/DIA), insulin-like growth factors (IGF-I and IGF-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in Frazzled proteins. Particularly domestic animals and thoroughbred horses in addition to humans are desired patients for such treatment with the SDF-5 proteins of the present invention.

The therapeutic method includes administering the composition topically, systemically, or locally as by injection or implantation. When administered, the therapeutic composition for use in this invention is, of course, in a pyrogen-free, physiologically acceptable form. Further, the composition may desirably be encapsulated or injected in a viscous form for delivery to the site of pancreatic or other tissue damage. Topical administration may be suitable for wound healing and tissue repair. Therapeutically useful agents other than the SDF-5 proteins which may also optionally be included in the composition as described above, may alternatively or additionally, be administered simultaneously or sequentially with the SDF-5 composition in the methods of the invention.

For implantation, the composition preferably includes a matrix capable of delivering human SDF-5 proteins to the site of pancreatic or other tissue damage, providing a structure for the developing tissue and optimally capable of being resorbed into the body. The matrix may provide slow release of human SDF-5 and/or other protein, as well as proper presentation and appropriate environment for cellular infiltration. Such matrices may be formed of materials presently in use for other implanted medical applications. The choice of matrix material is based on biocompatibility, biodegradability, mechanical properties, cosmetic appearance and interface properties. The particular application of the human SDF-5 compositions will define the appropriate formulation.

The dosage regimen will be determined by the attending physician considering various factors which modify the action of the human SDF-5 protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of human SDF-5 proteins in the composition. The addition of other known growth factors, such as IGF I (insulin like growth factor I), to the final composition, may also effect the dosage.

Progress can be monitored by periodic assessment of tissue growth and/or repair. The progress can be monitored, for example, x-rays, histomorphometric determinations and tetracycline labeling.

Uses and Biological Activity

The proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Proteins of the present invention can also be used as nutritional sources or supplements. Such uses include without limitation use as a protein or amino acid supplement, use as a carbon source, use as a nitrogen source and use as a source of carbohydrate. In such cases the protein of the invention can be added to the feed of a particular organism or can be administered as a separate solid or liquid preparation, such as in the form of powder, pills, solutions, suspensions or capsules. In the case of microorganisms, the protein of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1– 3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In *Current Protocols in Immunology*. J. E. e. a. Coligan eds. Vol 1 pp. 3.12.1–3.12.14, John Wiley and Sons, Toronto. 1994; and Measurement of mouse and human Interferon γ, Schreiber, R. D. In *Current Protocols in Immunology*. J. E. e. a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e. a. Coligan eds. Vol 1 pp. 6.3.1–6.3.12, John Wiley and Sons, Toronto. 1991; deVries et al., J. Exp. Med. 173: 1205–1211, 1991; Moreau et al., Nature 336:690–692, 1988; Greenberger et al., Proc. Natl. Acad. Sci. U.S.A. 80:2931–2938,1983; Measurement of mouse and human interleukin 6—Nordan, R. In *Current Protocols in Immunology*. J. E. e. a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In *Current Protocols in Immunology*. J. E. e. a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In *Current Protocols in Immunology*. J. E. e. a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II βchain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology*. J. E. e. a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, with out limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad. Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing,* pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: *Current Protocols in Immunology*, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169: 149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

The following examples illustrate practice of the present invention in recovering and characterizing human SDF-5 protein and employing the DNA to recover other SDF-5 proteins, obtaining the human proteins and expressing the proteins via recombinant techniques.

EXAMPLE 1

Cloning of a Human Homologue to Murine SDF-5

The nucleotide sequence of murine SDF-5 (personal communication, Professor Honjo) was used to query GenBank. Several EST's whose DNA sequence had been were identified at either the 5' or 3' end of the cDNA showed a high degree of identity with the murine SDF-5. Some of the EST's were from human sources. The various human EST's were aligned to the full-length murine SDF-5 nucleotide sequence, and it was determined that none of the clones from which the EST sequences were derived contained the entire coding sequence of SDF-5. The EST that aligned most 5' on the murine SDF-5 nucleotide sequence was H14917. This EST represented a 5' end DNA sequence of a human cDNA from breast tissue. The alignment with murine SDF-5 suggested that the human breast cDNA represented by EST #H14917 was missing approximately 147 nucleotides of coding sequence at the 5' end.

In order to attempt to isolate a full-length derivative of murine SDF-5, a biotinylated oligonucleotide probe (5'-biotin-ATCGATGCCGTGGCACAGCTGCAGGTTG-3' (SEQ ID NO: 7) was synthesized that represented the reverse complement of nucleotides 18 to 44 of the H14917 sequence. This probe was used in a solution enrichment protocol with 5 separate human full-length cDNA libraries made from the following tissues: adult lung, adult heart, adult kidney, fetal brain, and mammary gland. After the enrichment, about 60,000 colonies from each enriched library were plated onto 10 plates each, and subjected to standard colony hybridization techniques using the same oligonucleotide as a probe after labeling it with polynucleotide kinase and [g-$^{32}$P]ATP. Due to a technical problem, only 4 plates (24,000 colonies) were plated for the mammary gland library. Only the mammary gland library appeared to contain cDNA clones that hybridized to the probe. Twelve positive clones were picked, grown up and replated. These replated positives were then hybridized once again to the same probe to verify them and to assure their purity. All 12 of the initial positives gave hybridization signals upon secondary hybridization. Four of the candidates were subjected to DNA sequencing. A single clone was chosen (isolate #4) which was in the correct orientation, contained the entire coding sequence for human SDF-5, and whose sequence was verified by comparison with other isolates.

EXAMPLE 2

W-20 Bioassays

A. Description of W-20 Cells

Use of the W-20 bone marrow stromal cells as an indicator cell line is based upon the conversion of these cells to osteoblast-like cells after treatment with an osteogenic protein, such as a BMP protein [Thies et al, *Journal of Bone and Mineral Research,* 5:305 (1990); and Thies et al, *Endocrinology,* 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 µl of media (DME with 10% heat inactivated fetal calf serum, 2 mM glutamine and 100 Units/ml penicillin+100 µg/ml streptomycin. The cells are allowed to attach overnight in a 95% air, 5% $CO_2$ incubator at 37° C. The 200 µl of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 µl per well of calcium/magnesium free phosphate buffered saline and these washes are discarded. 50 µl of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 µl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 µl of 0.2 N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
|---|---|
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to pmoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of SDF-5 to BMP-2.

C. Osteocalcin RIA Protocol

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431 R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table III.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE 3

Rosen Modified Sampath-Reddi Assay

A modified version of the rat bone formation assay described in Sampath and Reddi, *Proc. Natl. Acad. Sci. USA*, 80:6591–6595 (1983) is used to evaluate bone and/or cartilage and/or other connective tissue activity of novel osteoinductive or chondroinductive proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, *Histology* (J B Lippincott Co. (1979), pp. 367–369, the disclosure of which is hereby incorporated by reference]. These findings may be reproduced in additional assays in which tendon/ligament-like tissues are observed in the SDF-5 protein containing implants. The SDF-5 proteins of this invention may be assessed for activity on this assay.

EXAMPLE 4

Expression of SDF-5

In order to produce murine, human or other mammalian SDF-5 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human SDF-5 is contemplated to be stably transformed mammalian cells.

One skilled in the art can construct mammalian expression vectors by employing the sequence of SEQ ID NO: 1, or other DNA sequences encoding SDF-5 protein or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 82:689–693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2 CXM is then constructed using loopout/in mutagenesis [Morinaga, et al., *Biotechnology* 84: 636 (1984). This removes bases 1075 to 1145 relative to the Hind III site near the SV40 origin of replication and enhancer sequences of pMT2. In addition it inserts the following sequence:

5'-PO-CATGGGCAGCTCGAG-3' (SEQ ID NO: 4)

at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform *E. Coli* HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR:

```
                                         (SEQ ID NO: 5)
CTGCAGGCGAGCCTGAATTCCTCGAGCCATCATG-3'
            PstI        Eco RI XhoI
```

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECATI [S. K. Jung, et al, *J. Virol* 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

```
                                                                        (SEQ ID NO: 6)
5'-CGAGGTTAAAAAACGTCTAGGCCCCCCGAACCACGGGGACGTGGTTTTCCTTT
   TaqI

GAAAAACACGATTGC-3'
          XhoI
```

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRI-TaqI fragment, and the 68 bp oligonucleotide adapter TaqI-16hoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and P-lactamase markers and an EMC sequence, in appropriate relationships to direct the high level expression of the desired cDNA in mammalian cells.

The construction of vectors may involve modification of the SDF-5 DNA sequences. For instance, SDF-5 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of SDF-5 proteins. Additionally, the sequence of SEQ ID NO:1 or other sequences encoding SDF-5 proteins can be manipulated to express a mature SDF-5 protein by deleting SDF-5 propeptide sequences and replacing them with sequences encoding the complete propeptides of other secreted proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified SDF-5 coding sequence could then be inserted into a known bacterial vector using procedures such as described in T. Taniguchi et al., *Proc. Natl. Acad. Sci. USA*, 77:5230–5233 (1980). This exemplary bacterial vector could then be transformed into bacterial host cells and a SDF-5 protein expressed thereby. For a strategy for producing extracellular expression of SDF-5 proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a SDF-5 protein of the invention in mammalian cells may involve the construction of cells containing multiple copies of the heterologous SDF-5 gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a SDF-5 protein of the invention in operative association with other plasmid sequences enabling expression thereof and the DHFR expression plasmid pAdA26SV(A)3 [Kaufman and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 μM MTX) as described in Kaufman et al., *Mol Cell Biol.*, 5:1750 (1983). Transformants are cloned, and biologically active SDF-5 expression is monitored by the Rosen-modified Sampath-Reddi rat bone formation assay described above in Example 3. SDF-5 protein expression should increase with increasing levels of MTX resistance. SDF-5 polypeptides are characterized using standard techniques known in the art such as pulse labeling with [35S] methionine or cysteine and polyacrylamide gel electrophoresis. Similar procedures can be followed to produce other related proteins.

EXAMPLE 5

Biological Activity of Expressed SDF-5

To measure the biological activity of the expressed SDF-5 proteins obtained in Example 4 above, the proteins are recovered from the cell culture and purified by isolating the SDF-5 proteins from other proteinaceous materials with which they are co-produced as well as from other contaminants. The purified protein may be assayed in accordance with the rat bone formation assay described in Example 3 and other assays described herein.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

EXAMPLE 6

Using Northern analysis, SDF-5 proteins can be tested for their effects on various cell lines. Suitable cell lines include cell lines derived from E13 mouse limb buds. After 10 days of treatment with SDF-5 protein, the cell phenotype is examined histologically for indications of tissue differentiation. In addition, Northern analysis of mRNA from SDF-5 protein treated cells can be performed for various markers including one or more of the following markers for bone, cartilage and/or tendon/ligament, as described in Table IV:

TABLE IV

| Marker | Bone | Cartilage | Tendon/Ligament |
| --- | --- | --- | --- |
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels

EXAMPLE 7

Expression Analysis

In situ hybridization was used to localize SDF-5 mRNA in sections 10.5–15.5 dpc mouse embryos. SDF-5 was expressed in the developing joints of the appendicular skeleton and in some tendons and ligaments. No expression was detected in the bones of the axial or appendicular skeleton or in muscle. These obvious observations strongly implicated SDF-5 in connective tissue formation. From these results, it seemed most likely that cartilage formation would be regulated by SDF-5, and this information was the basis for evaluating this protein using in vitro assays.

In vitro Activity

Murine SDF-5 was expressed in CHO cells. MLB13MYC-clone 14 cells were grown to confluence and treated with either SDF-5, BMP-2, a combination of SDF-5 and BMP-2, or untreated. SDF-5-containing CHO conditioned media was used at a 1:20 dilution (~10 ng/ml final concentration), and mock conditioned media from CHO cells was added to BMP-2 and untreated cell cultures, BMP-2 was used at 100 ng/ml. After four days, RNA was harvested and gene expression analyzed by a GeneChip 50 Scanner (Affymetrix). In untreated or SDF-5 treated cells there was no detectable expression of genes characteristic of a bone or cartilage phenotype. BMP-2 induced the expression of hypertrophic cartilage and bone marker genes, together with low cartilaginous markers. In cells treated with a combination of both SDF-5 and BMP-2 bone (Osteocalcin; alkaline phosphatase; PTH/PTHrP receptor) and hypertrophic cartilage markers (Type X collagen) were significantly decreased or absent, and markers for cartilage (Collagen Types II and IX; decorin; aggrecan) were increased, compared with BMP-2 alone. This effect is similar to that previously observed for combinations of PTHrP and BMP-2, except there seems to be a greater enhancement of cartilage phenotype with the SDF-5 combination.

EXAMPLE 8

Embryonic Stem Cell Assay

In order to assay the effects of the SDF-5 proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified human SDF-5 protein produced by the steps of
   (a) culturing a cell transformed with a DNA comprising the nucleotide sequence from nucleotide #316 to #1143 as shown in SEQ ID NO: 1; and
   (b) recovering and purifying from said culture medium a protein comprising the amino acid sequence from amino acid #21 to amino acid #295 as shown in SEQ ID NO: 2.

2. A purified human SDF-5 protein comprising the amino acid sequence from amino acid #1 to #295 of SEQ ID NO: 2.

3. A purified human SDF-5 protein comprising the amino acid sequence from amino acid #1 to #275 of SEQ ID NO: 3.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2027 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GAATTCGGCC TTCATGGCCT AGCTCATTCT GCTCCCCCGG GTCGGAGCCC CCCGGAGCTG      60
CGCGCGGGCT TGCAGCGCCT CGCCCGCGCT CCTCCCGGTG TCCCGCTTCT CCGCGCCCCA     120
GCCGCCGGCT GCCAGCTTTT CGGGGCCCCG AGTCGCACCC AGCGAAGAGA GCGGGCCCGG     180
GACAAGCTCG AACTCCGGCC GCCTCGCCCT TCCCCGGCTC CGCTCCCTCT GCCCCCTCGG     240
GGTCGCGCGC CCACGATGCT GCAGGGCCCT GGCTCGCTGC TGCTGCTCTT CCTCGCCTCG     300
CACTGCTGCC TGGGCTCGGC GCGCGGGCTC TTCCTCTTTG CCAGCCCGA CTTCTCCTAC      360
AAGCGCAGCA ATTGCAAGCC CATCCCGGCC AACCTGCAGC TGTGCCACGG CATCGAATAC     420
CAGAACATGC GGCTGCCCAA CCTGCTGGGC ACGAGACCA TGAAGGAGGT GCTGGAGCAG      480
GCCGGCGCTT GGATCCCGCT GGTCATGAAG CAGTGCCACC CGGACACCAA GAAGTTCCTG     540
TGCTCGCTCT TCGCCCCCGT CTGCCTCGAT GACCTAGACG AGACCATCCA GCCATGCCAC     600
TCGCTCTGCG TGCAGGTGAA GGACCGCTGC GCCCCGGTCA TGTCCGCCTT CGGCTTCCCC     660
TGGCCCGACA TGCTTGAGTG CGACCGTTTC CCCCAGGACA ACGACCTTTG CATCCCCCTC     720
GCTAGCAGCG ACCACCTCCT GCCAGCCACC GAGGAAGCTC CAAAGGTATG TGAAGCCTGC     780
AAAAATAAAA ATGATGATGA CAACGACATA ATGGAAACGC TTTGTAAAAA TGATTTTGCA     840
CTGAAAATAA AAGTGAAGGA GATAACCTAC ATCAACCGAG ATACCAAAAT CATCCTGGAG     900
ACCAAGAGCA AGACCATTTA CAAGCTGAAC GGTGTGTCCG AAAGGGACCT GAAGAAATCG     960
GTGCTGTGGC TCAAAGACAG CTTGCAGTGC ACCTGTGAGG AGATGAACGA CATCAACGCG    1020
CCCTATCTGG TCATGGGACA GAAACAGGGT GGGGAGCTGG TGATCACCTC GGTGAAGCGG    1080
TGGCAGAAGG GGCAGAGAGA GTTCAAGCGC ATCTCCCGCA GCATCCGCAA GCTGCAGTGC    1140
TAGTCCCGGC ATCCTGATGG CTCCGACAGG CCTGCTCCAG AGCACGGCTG ACCATTTCTG    1200
CTCCGGGATC TCAGCTCCCG TTCCCCAAGC ACACTCCTAG CTGCTCCAGT CTCAGCCTGG    1260
GCAGCTTCCC CCTGCCTTTT GCACGTTTGC ATCCCCAGCA TTTCCTGAGT TATAAGGCCA    1320
CAGGAGTGGA TAGCTGTTTT CACCTAAAGG AAAAGCCCAC CCGAATCTTG TAGAAATATT    1380
CAAACTAATA AAATCATGAA TATTTTTATG AAGTTTAAAA ATAGCTCACT TTAAAGCTAG    1440
TTTTGAATAG GTGCAACTGT GACTTGGGTC TGGTTGGTTG TTGTTTGTTG TTTTGAGTCA    1500
GCTGATTTTC ACTTCCCACT GAGGTTGTCA TAACATGCAA ATTGCTTCAA TTTTCTCTGT    1560
GGCCCAAACT TGTGGGTCAC AAACCCTGTT GAGATAAAGC TGGCTGTTAT CTCAACATCT    1620
TCATCAGCTC CAGACTGAGA CTCAGTGTCT AAGTCTTACA ACAATTCATC ATTTTATACC    1680
TTCAATGGGA ACTTAAACTG TTACATGTAT CACATTCCAG CTACAATACT TCCATTTATT    1740
AGAAGCACAT TAACCATTTC TATAGCATGA TTTCTTCAAG TAAAAGGCAA AAGATATAAA    1800
```

```
TTTTATAATT GACTTGAGTA CTTTAAGCCT TGTTTAAAAC ATTTCTTACT TAACTTTTGC    1860

AAATTAAACC CATTGTAGCT TACCTGTAAT ATACATAGTA GTTTACCTTT AAAAGTTGTA    1920

AAAATATTGC TTTAACCAAC ACTGTAAATA TTTCAGATAA ACATTATATT CTTGTATATA    1980

AACTTTACAT CCTGTTTTAC CTAAAAAAAA AAAAAAAAG CGGCCGC                  2027
```

(2) INFORMATION FOR SEQ ID NO:2:

(i) SEQUENCE CHARACTERISTICS:
        (A) LENGTH: 295 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295
```

(2) INFORMATION FOR SEQ ID NO:3:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Ser Ala Arg Gly Leu Phe Leu Phe Gly Gln Pro Asp Phe Ser Tyr Lys
 1               5                  10                  15

Arg Ser Asn Cys Lys Pro Ile Pro Ala Asn Leu Gln Leu Cys His Gly
             20                  25                  30

Ile Glu Tyr Gln Asn Met Arg Leu Pro Asn Leu Leu Gly His Glu Thr
         35                  40                  45

Met Lys Glu Val Leu Glu Gln Ala Gly Ala Trp Ile Pro Leu Val Met
 50                  55                  60

Lys Gln Cys His Pro Asp Thr Lys Lys Phe Leu Cys Ser Leu Phe Ala
 65                  70                  75                  80

Pro Val Cys Leu Asp Asp Leu Asp Glu Thr Ile Gln Pro Cys His Ser
                 85                  90                  95

Leu Cys Val Gln Val Lys Asp Arg Cys Ala Pro Val Met Ser Ala Phe
            100                 105                 110

Gly Phe Pro Trp Pro Asp Met Leu Glu Cys Asp Arg Phe Pro Gln Asp
        115                 120                 125

Asn Asp Leu Cys Ile Pro Leu Ala Ser Ser Asp His Leu Leu Pro Ala
130                 135                 140

Thr Glu Glu Ala Pro Lys Val Cys Glu Ala Cys Lys Asn Lys Asn Asp
145                 150                 155                 160

Asp Asp Asn Asp Ile Met Glu Thr Leu Cys Lys Asn Asp Phe Ala Leu
                165                 170                 175

Lys Ile Lys Val Lys Glu Ile Thr Tyr Ile Asn Arg Asp Thr Lys Ile
            180                 185                 190

Ile Leu Glu Thr Lys Ser Lys Thr Ile Tyr Lys Leu Asn Gly Val Ser
        195                 200                 205

Glu Arg Asp Leu Lys Lys Ser Val Leu Trp Leu Lys Asp Ser Leu Gln
210                 215                 220

Cys Thr Cys Glu Glu Met Asn Asp Ile Asn Ala Pro Tyr Leu Val Met
225                 230                 235                 240

Gly Gln Lys Gln Gly Gly Glu Leu Val Ile Thr Ser Val Lys Arg Trp
                245                 250                 255

Gln Lys Gly Gln Arg Glu Phe Lys Arg Ile Ser Arg Ser Ile Arg Lys
            260                 265                 270

Leu Gln Cys
        275
```

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CATGGGCAGC TCGAG                                                        15

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CTGCAGGCGA GCCTGAATTC CTCGAGCCAT CATG                                   34

(2) INFORMATION FOR SEQ ID NO:6:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCCCTGTGGG TAGAACGAGG TTAAAAAACG TCTAGGCCCC CCGAACCACG GGGACGTGGT       60

TTTCCTTTGA AAAACACGAT TGC                                               83
```